United States Patent [19]

Nakama

[11] 4,300,941
[45] Nov. 17, 1981

[54] AGENT AND METHOD FOR ACCELERATING THE MATURATION OF FIELD AND GARDEN CROPS

[75] Inventor: Kazumitsu Nakama, Yaizu, Japan

[73] Assignee: Showa Denko Kabushiki Kaisha, Tokyo, Japan

[21] Appl. No.: 138,189

[22] Filed: Apr. 7, 1980

[30] Foreign Application Priority Data

Apr. 19, 1979 [JP] Japan .................................. 54-47376
Dec. 4, 1979 [JP] Japan ................................ 54-157074

[51] Int. Cl.$^3$ ............................................ A01N 59/02
[52] U.S. Cl. ...................................................... 71/65
[58] Field of Search ............................................ 71/65

[56] References Cited

U.S. PATENT DOCUMENTS 1,803,157  4/1931  Wesenberg et al. ..................... 71/65

Primary Examiner—Catherine L. Mills
Attorney, Agent, or Firm—McAulay, Fields, Fisher, Goldstein & Nissen

[57] ABSTRACT

An agent and method for accelerating the maturation of field and garden crops from which fruits, seeds, roots or subterranean stems are harvested are presented. The maturation accelerating agent comprises one or more thiosulfates such as potassium thiosulfate, sodium thiosulfate, magnesium thiosulfate and ammonium thiosulfate. The application of thiosulfates in the form of, for example, an aqueous solution to the field and garden crops results in the effective acceleration of the maturation of the crops.

2 Claims, 1 Drawing Figure

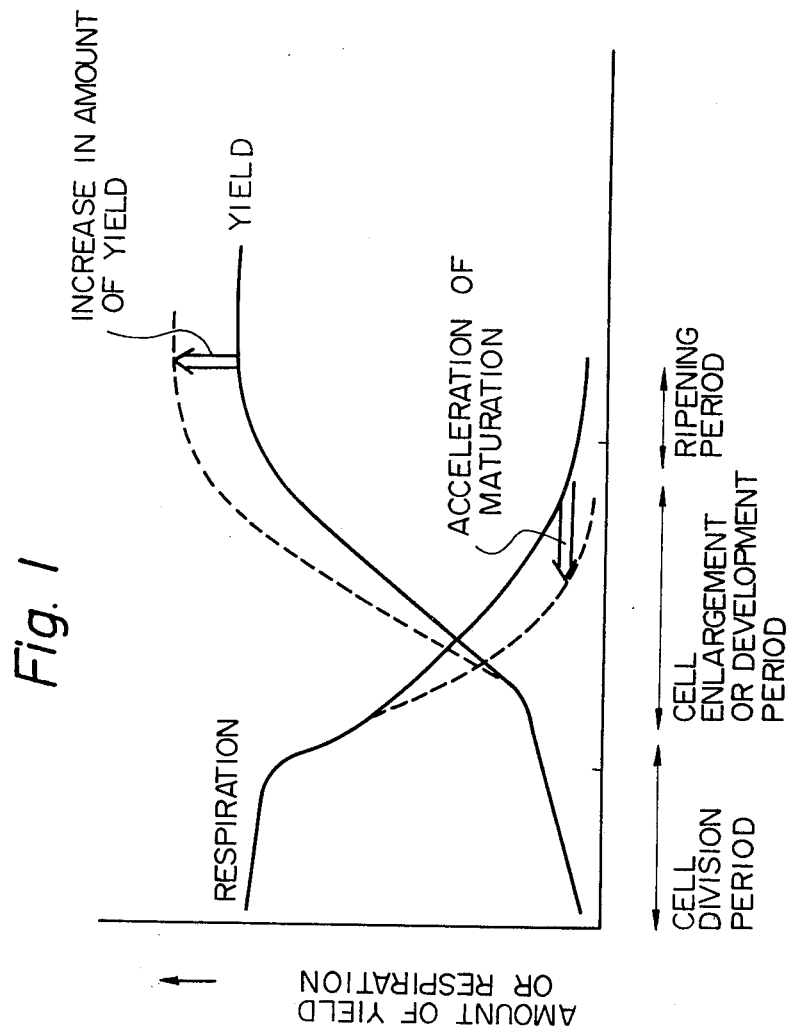

AGENT AND METHOD FOR ACCELERATING THE MATURATION OF FIELD AND GARDEN CROPS

BACKGROUND OF THE INVENTION (1) Field of the Invention

The present invention relates to an agent for accelerating the maturation of field and garden crops from which fruits, seeds, roots or subterranean stems are harvested. The present invention also relates to a method for accelerating the maturation of field and garden crops from which fruits, seeds, roots or subterranean stems are harvested.

(2) Description of the Prior Art

There is considerable interest among cultivators of field and garden crops in the early harvesting of the crops, the increasing the crop yields and the improvement of crops qualities, such as sugar content, acidity, color, starch content and protein content.

Heretofore, in order to accelerate the maturation of fruit trees and fruit vegetables, the surfaces of leaves and fruits of fruit trees and fruit vegetables were sprayed with or the harvested fruits were fumigated with substances having a respiration poisoning effect, such as lead arsenate, gaseous hydrocyanic acid and the like. Although such spraying and fumigating are effective, there were problems in these methods in that prematured fruits not having good quality were occasionally obtained and the growth of the fruits is stopped due to the fact that the physiology of the plants are changed by the use of said substances, and also, that a slight amount of arsenic or hydrocyanic acid, which is toxic, is likely to remain in the fruits.

In order to accelerate the maturation of field and garden crops, it is also known that the surfaces of leaves and fruits of plants are sprayed with lime sulfur or the mixture of phosfate solution therewith. However, this method has a problem in that, since the white powders of the above-mentioned agents are adhered to, for example, the surface of the fruits after the treatment, the market value thereof are decreased.

Furthermore, the market value of citrus fruits, such as tangerines (or Unshu mandarin oranges), navel oranges and Iyo oranges, is influenced by the size, shape, color and sweetness thereof. Among these, the sweetness is most important for the market value of citrus fruits. It is known that the sweetness of the citrus fruit mainly depends on the sugar content of the fruit and, in turn, the sugar content increases with an increase in the content of carotinoid type pigments contained in the epidermis of the fruits (i.e. with the increase in redness of the epidermis). Thus, the degree of redness of the epidermis of citrus fruits is an important factor which determines the market value thereof. It is, therefore, desired that the early harvesting of citrus fruits and the early coloring of citrus fruits can be simultaneously achieved.

SUMMARY OF THE INVENTION

Accordingly, an object of the present invention is to obviate the above-mentioned problems of the prior arts and to provide an agent and a method for accelerating the maturation of field and garden crops from which fruits, seeds, roots or subterranean stems are harvested.

Another object of the present invention is to provide a maturation accelerating agent for the above-mentioned crops which is not toxic, which does not adversely affect the natural physiology of the plants, which does not reduce the market value of the harvested crops and which improves the quality of the harvested crops.

Other objects and advantages of the present invention will be apparent from the following description.

In accordance with the present invention, there is provided an agent for accelerating the maturation of field and garden crops from which fruits, seeds, roots or subterranean stems are harvested, said agent comprising at least one thiosulfate.

In accordance with the present invention, there is further provided a method for promoting the maturation of field and garden crops from which fruits, seeds, roots or subterranean stems are harvested, said method comprising applying at least one thiosulfate to the crops.

BRIEF DESCRIPTION OF THE DRAWING

The present invention will be better understood from the description set forth below with reference to the accompany drawing of FIG. 1, which is a graph schematically illustrating the correlations between the maturation of fruits and the respiration and yield of fruits. In FIG. 1, the solid lines represents the conventional correlations and the dotted lines represent the correlations when the present invention is applied.

DETAILED DESCRIPTION OF THE INVENTION

The field and garden crops which can be accelerated by the application of thiosulfates thereto include, for example: fruit trees, such as apples, pears, peaches, persimmons, chestnuts, oranges (e.g. mandarin oranges, navel oranges, Iyo oranges, summer oranges and Hassaku oranges), loquats (or Japanese medlars), cherries, apricots, plums, walnuts, figs, olives, almonds and the like; fruit vines such as grapes and the like; fruit vegetables, such as Cucurbitaceae crops (e.g. cucumbers, squashes, water melons and melons), Solanaceae crops (e.g. egg-plants, tomatoes and Spanish paprikas), strawberries and the like; edible roots, such as root crops (e.g. Japanese radishes, sugar beets, turnips, carrots, burdocks and horseradishes (i.e. Eutrema wasabi), tuber crops (e.g. potatoes, sweet potatoes, yams (i.e. Dioscorea), toroes, Jerusalem artichokes, konnyaku-imo, lotus roots, arrow heads and gingers) and the like; pulse crops, such as soyabeans, azuki beans, peas, broad beans, kidney beans, peanuts, cowpeas and the like; grains and feed crop plants such as rice plants, wheat, barley, lye, oats, buckwheat, German millet, sawa millet, corn, and the like, and; other crop plants such as coffee, cocoa, pepper, seasame, rapeseed, castor beans, cotton and the like.

Although various kinds of thiosulfates can be used for accelerating the maturation of field and garden crops, potassium thiosulfate, sodium thiosulfate, magnesium thiosulfate and ammonium thiosulfate are preferable from the practical point of view. According to the present invention, the thiosulfates are mainly dressed to the foliage generally in the form of aqueous solutions. Although the application time of the thiosulfate to plants depends on the variety of the plant to which it is applied, it is preferable that the thiosulfates be dressed to the foliage in two or three portions, separated by intervals of 5 through 10 days, immediately before the change of stage in plant physiology between the nutritive growth stage and the maturation stage. For instance, in the case of mandarin oranges, the thiosulfates are most preferably dressed to mainly the foliage of the orange trees in the form of the aqueous solutions when the tops of the fruits begin to degreen.

The concentration of the aqueous thiosulfate solutions used in the present invention may be varied over a wide range depending upon the variety of the plant to which they are applied, the plant stage, the weather conditions and the like. However, generally speaking, when the concentration of the aqueous thiosulfate solution is too low, desirable maturation accelerating effects can not be obtained. Contrary to this, when said concentration is too high, it is possible that phytotoxicity may be generated. Accordingly, it is preferable that the aqueous thiosulfate solution be applied in a concentration of from approximately 0.01 to approximately 0.3% by weight. However, the application amounts of the aqueous thiosulfate solutions may be varied over a wide range depending upon, for example, the variety of the plant to which they are applied. For instance, in the case of fruit trees or fruit vegetables, the aqueous thiosulfate solutions are preferably sprayed in an amount of from approximately 200 to approximately 1,000 liters per 10 ares of the field or garden.

The thiosulfates employed, as an active ingredient, in the maturation accelerating agent of the present invention are water-soluble inorganic salts and, as sodium thiosulfate is used as a food additive, the thiosulfates are not toxic to men and beasts. Furthermore, potassium thiosulfate and ammonium thiosulfate can be easily oxidized to potassium sulfate and ammonium sulfate, respectively. It is well-known that these sulfates can be used as a chemical fertilizer. Thus, even in the case where the thiosulfate solutions are adhered to clothes during their application or in the case where the thiosulfate solutions spread into the soil after their application due to, for example, rain, no problems result in human beings, cattle, plant crops or the natural environment.

According to the present invention, the maturation of the field and garden crops from which fruits, seeds, roots or subterranean stems are harvested can be effectively accelerated without causing any adverse affects on the natural physiology of the plant crops. The action of the thiosulfates for accelerating the maturation of the field and garden crops is not clearly understood, but it would seem that, without prejudice in the present invention, the thiosulfates modify the physiology of the crops in a manner such that the amount of growth is increased and the maturation is accelerated as mentioned hereinbelow.

A portion of the carbohydrates, such as starch, formed in the surfaces of the leaves of plants by photosynthesis is utilized for the development and metabolization of the leaves themselves. Most of the remainder of the formed carbohydrates is transferred from the leaves to the other portions of the plants. A portion of the transferred carbohydrates is consumed with respiration (i.e. energy metabolism) and is also utilized for the formation of new tissues and organs. The remainder of the transferred carbohydrates is accumulated as a reserve substance. The reserve substances (i.e. products of assimilation) thus accumulated in the plants are harvested as crops. Based on portions which are harvested as crops, the crops are classified into the groups of, for example, fruit trees and fruit vegetables from which fruits are harvested, grains and pulse crops from which hymenocarps are harvested, tuber crops from which roots or subterranean stems are harvested and leaf crops from which leaves or stems are harvested. However, the distribution and degree of the transfer of the products of assimilation vary with the physiology of plants, growth cycle or stages and the like. For example, in the nutritive growth stage after the germination or the development of new buds, a large amount of carbohydrates are transferred to organs of nutrition such as roots, stems and leaves and, in the genital development stage, a large amount of carbohydrates are transfered to genital organs such as flowered and fructificated fruits. These carbohydrates are utilized for the growth and enlargement of each organ. The enlargement of seeds and fruits (i.e. the accumulation of the products of assimilation therein) and the nutritive growth stage simultaneously occur. However, the genital development antagonize the nutritive growth stage at a certain time. The transfer of from the nutritive growth stage to the genital development stage and the accumulation of the transferred products of assimilation (e.g. the correlation between the elongation and its termination, and the flowering and the enlargement of fruits) are relatively clear with respect to fruit trees and Gramineae plants. However, the nutritive growth and the genital development simultaneously occur with respect to fruit vegetables belonging to, for example, Solanaceae and Cucurbitaceae plants such as tomatoes and cucumbers. States at which the amount of the products of assimilation becomes larger than the amount of the consumption and the development of the organs approximately reaches the limits thereof are generally called "maturation" or "ripening". In the case of root vegetables, the products of assimilation are mainly accumulated in roots, tubers and subterranean stems, so that the roots, the tubers and the subterranean stems are enlarged. In the case of grains and pulse crops, hymenocarps are enriched due to the accumulation of the products of assimilation. In the case of fruit trees and fruit vegetables, fruits are enlarged and the sugar content and the color thereof are increased due to the accumulation of the products of assimilation. At the end of this process the fruits are said to be "ripe". In this state, the amount of the respiration of plants is minimized. Except for leaf vegetables and other special crops, well-developed nutrition organs and matured fruits and seeds are generally harvested as field and garden crops. For this reason, the change in the amount of the respiration and the transfer of the products of assimilation are important for the cultivation of field and garden crops.

Typical correlations between the maturation of fruits, and the respiration and growth of fruits will now be explained with reference to FIG. 1. As indicated by the solid lines of FIG. 1, which represent the conventional correlations between the maturation of fruits, and the resperation and yield of fruits, in a cell division period the amount of the respiration in large and a substantial amount of the products of assimilation is consumed for the growth of the plant. Therefore, the amount of the products of assimilation which is transferred to fruits is very small in a cell division period. However, in a cell enlargement or development period, the amount of the respiration decreases and, therefore, the products of assimilation are mainly transferred to fruits and reserved as nourishment in organs which enlarges the fruits. After that the fruits are matured in a ripening period.

Contrary to the above, in the case where the thiosulfates is applied to plants, the correlations between the maturation of fruits, and the respiration and growth of fruits are changed as indicated by dotted lines of FIG. 1. Thus, since it is believed that the thiosulfates accelerates the decrease in the respiration based on the natural plant physiolosy, the respiration curve changes as indicated by the dotted line of FIG. 1 and, accordingly, the growth curve also changes as indicated by the dotted line of FIG. 1. As a result, it is believed that the maturation or ripening period is accelerated (i.e. the harvesting time is shortened) and the amount of growth (i.e. the yield) is increased. It should be noted that, since the effects of the applied thiosulfates are temporary and the thiosulfates do not change the original plant physiology, the plants to which the thiosulfates are applied can be grown without causing any excessive suppression and change in the original plant physiology. Therefore, even in the case where the maturation of fruits should be accelerated, while the nutritive growth is allowed (as in the case of tomatoes and cucumbers), the entire plants can be grown without losing a balance between the acceleration and the growth.

According to the present invention, the maturation of cultivated crop plants can be accelerated by the application of thiosulfates, so that the harvesting season shortened and the harvesting yield can be increased. In addition, according to the present invention, the qualities of the harvested field and garden crops, such as the sugar content, the acid strength, the contents of starches and proteins, the color and the like can be turned in favor by the increase in the amount of growth.

The present invention is further illustrated by, but is by no means limited to, the following examples, in which all percentages are expressed on a weight basis unless otherwise specified.

Example 1

The coloring acceleration effects of the various agents listed in Table 1 below were evaluated in an orchard wherein 60 trees per 10a of fifteen year old Aoshima Unshu, mandarin orange trees were planted. On different test areas, each having two trees, each diluted agent shown in Table 1 was uniformly sprayed in an amount corresponding to 700 l/10a. The spraying was first carried out when the tops of the fruit began to degreen and, after ten days, the spraying was further carried out in one group of area. In another group of area, the spraying was only carried out when the tops of the fruit began to degreen.

TABLE 1

| Sample Agent | | Concentration (%) | Dilution (times) |
| --- | --- | --- | --- |
| A$_1$ | (NH$_4$)$_2$S$_2$O$_3$ | 55.7 | 300 |
| A$_2$ | (NH$_4$)$_2$S$_2$O$_3$ | 55.7 | 200 |
| B$_1$ | K$_2$S$_2$O$_3$ | 55.7 | 300 |
| B$_2$ | K$_2$S$_2$O$_3$ | 55.7 | 200 |
| C$_1$ | Na$_2$S$_2$O$_3$ | 55.7 | 300 |
| C$_2$ | Na$_2$S$_2$O$_3$ | 55.7 | 200 |
| R | Commercially available lime sulfur | 45 | 100 |

Approximately 10% of the harvested fruit was randomly collected and the degree of color of the epidermis of the fruit was determined by using a differential colorimater. Averages of the results are shown in Table 2 below.

In Table 2, L represents brightness a and b represent red and green color indexes, respectively, and a/b represents the degree of red color.

TABLE 2

| Sample Agent | Number of Times of Spraying | Degree of Color | | | |
| --- | --- | --- | --- | --- | --- |
| | | L | a | b | a/b |
| A$_1$ | 1 | 57.0 | 27.7 | 32.2 | 0.86 |
| | 2 | 57.2 | 28.4 | 31.9 | 0.89 |
| A$_2$ | 1 | 57.2 | 27.9 | 32.1 | 0.87 |
| | 2 | 56.5 | 30.4 | 32.0 | 0.95 |
| B$_1$ | 1 | 57.2 | 27.8 | 31.6 | 0.88 |
| | 2 | 57.5 | 29.6 | 31.1 | 0.95 |
| B$_2$ | 1 | 58.0 | 30.3 | 32.2 | 0.94 |
| | 2 | 56.6 | 31.7 | 31.4 | 1.01 |
| C$_1$ | 1 | 57.5 | 26.9 | 30.9 | 0.87 |
| | 2 | 57.2 | 29.1 | 31.6 | 0.91 |
| C$_2$ | 1 | 57.3 | 29.9 | 32.8 | 0.89 |
| | 2 | 57.0 | 31.2 | 31.5 | 0.97 |
| R* | 2 | 58.4 | 26.5 | 30.8 | 0.86 |

*Since a large amount of white powder was adhered to the surface of the fruit, the determination was carried out after the white powder was removed with dry cloth.

Example 2

On eggplants (variety: Senryo #2) planted in a field aqueous sodium thiosulfate, potassium thiosulfate and potassium sulfate solutions were sprayed to evaluate the maturation acceleration effect of each agent on the eggplants. An aqueous solution, containing 20 l of water of each agent in an amount listed in Table 3 below was separately applied to the surfaces of the leaves of the eggplants planted in a 1a area.

The eggplants were planted on May 9 and pruned on July 25. A fertilizer containing 15% of N, 15% of P$_2$O$_5$ and 15% of K$_2$O was applied to the field in an amount of 10 kg/a on May 7 and, furthermore, on June 30, July 28 and August 30, a urea fertilizer was additionaly applied in an amount of 1 kg/a in each time. The sample agents were applied to the surfaces of the leaves of the eggplants every ten days from June 20 (i.e. the first harvesting date) till 10 days before October 8 (i.e. the final harvesting date). The amounts of the sprayed agents in each spraying were as follows:

TABLE 3

| Sample Agent | Amount (g/each time) | S$_2$O$_3$ Content (g) | K$_2$O Content (g) |
| --- | --- | --- | --- |
| Sodium thiosulfate (Na$_2$S$_2$O$_3$ . 5H$_2$O) | 95 | 42.9 | — |
| Potassium thiosulfate (K$_2$S$_2$O$_3$ . ½H$_2$O) | 75 | 42.8 | 36.0 |
| Potassium sulfate* (K$_2$SO$_4$) | 67 | — | 36.2 |

*Comparative sample

The yields obtained from the sprayed area and from a control area in which no agent was sprayed are shown in the following Table 4.

TABLE 4

| Yield | Control Section | Potassium Sulfate | Potassium Thiosulfate | Sodium Thiosulfate |
| --- | --- | --- | --- | --- |
| Total Yield (kg/a) | 456.3 | 463.3 | 524.2 | 493.6 |
| % | 100 | 102 | 115 | 108 |

As is clear from the results shown in Table 4, the yields in the thiosulfate sprayed areas were higher than the yield in the control area and the yield in the area sprayed with K$_2$O (i.e. a fertilizing component) was also higher than the yield in the control area. Specifically, the effect obtained in the area sprayed with potassium thiosulfate containing both $S_2O_3^{--}$ and $K_2O$ is synergetic compared to the effects obtained in the area sprayed with $S_2O_3^{--}$ and in the area sprayed with $K_2O$.

Example 3

The maturation accelerating effect of potassium thiosulfate on cucumbers (variety: Tokiwa Hikari #3P) was evaluated in a field wherein the cucumbers were planted in five areas. Two lines, of 10 cucumbers each, were planted 50 cm apart in each area. An aqueous potassium thiosulfate solution, prepared by diluting a 30% by weight aqueous potassium thiosulfate solution with water by a factor of 200, was applied to the surfaces of the leaves of the cucumbers in each area.

The cucumbers were planted on April 10 after dressing a basic fertilizer containing 160 g of N, 333 g of $P_2O_5$ and 160 g of $K_2O$ and, then, on May 10, June 10 and July 10, a fertilizer containing 80 g of N and 80 g of $K_2O$ was additionally applied. The aqueous potassium thiosulfate solution was applied to the surfaces of the leaves of the cucumbers in an amount of 2.7 liters on each of the days shown in Table 5 below. The total yield obtained from each of the cultivated areas is shown in Table 5.

TABLE 5

| Cultivation | | Yield | |
| --- | --- | --- | --- |
| area | Spraying Date | (g) | (%) |
| 1 | May 20 and 30 | 92.8 | 100 |
| 2 | June 10 and 20 | 100.7 | 108 |
| 3 | June 30 and July 10 | 114.3 | 123 |
| 4 | July 20 and July 30 | 105.3 | 113 |
| 5* | No spraying | 93.2 | 100 |

*Control (no thiosulfate was applied)

Although there was no remarkable difference in quality between the harvested cucumbers from the five areas, except for the area 1 in which the thiosulfate was applied on May 20 and 30. The yields obtained from the areas 2, 3 and 4 were higher than that obtained from the control area. Specifically, the high yield of area 3, in which the thiosulfate was applied on June 30 and July 10, was remarkable.

Example 4

Soybeans (variety: Enrei) were seeded on June 12, and a 0.15% aqueous potassium thiosulfate solution was applied on surfaces of the leaves of the soybean plants by using a spray machine on August 10 and September 10, in such a manner that the entire surfaces of the leaves were uniformly wetted. The soybeans were harvested on October 17. The fertilizer was applied in a conventional manner. The results are shown in the following Table 6.

TABLE 6

| | Soybean Yield | | | | | |
| --- | --- | --- | --- | --- | --- | --- |
| | Total Yield | | | | Soybean (Yield /Total | Off Grade Yield |
| Area | (kg/10 a) | (%) | (kg/10 a) | (%) | Yield) | (kg/10 a) |
| Control area | 862 | 100 | 351 | 100 | 0.407 | 10.1 |
| Sprayed area | 880 | 102 | 378 | 107 | 0.429 | 4.9 |

As is clear from the results shown in Table 6, the soybean yield was increased and the off grade yield was decreased in the sprayed area compared to those in the control area.

(Remarks: The fertilization in each Example hereinbelow was also carried out in a conventional manner.)

Example 5

Potatoes (variety: Tejima) were seeded on March 1 and a 0.15% aqueous potassium thiosulfate solution was applied to the entire surfaces of the leaves of the potatoe plants on May 25 and June 10 in a manner as described in Example 4. The potatoes were harvested on June 19. After that, the maturation acceleration effect of potassium thiosulfate was evaluated with respect to the potatoes.

The results are shown in the following Table 7.

TABLE 7

| | Weight of Stems and Leaves | | Weight of Good Potatoes | | | | | Weight of Off-Grade |
| --- | --- | --- | --- | --- | --- | --- | --- | --- |
| Area | (kg/a) | (%) | L(>120 g) | M(60-120 g) | S(<60 g) | Total | (%) | (kg/a) |
| Control Area | 120 | 100 | 130 | 80 | 45 | 255 | 100 | 14 |
| Sprayed Area | 128 | 107 | 135 | 111 | 27 | 273 | 107 | 5 |

As is clear from the results shown in Table 7 above, compared to the control area, the weight of good potatoes and, especially, the ratios of the large grades L and M were increased, and the weight of off-grade was decreased in the sprayed area.

Example 6

Peanuts (variety: Tachimasari) were seeded on May 12 and a 0.15% aqueous potassium thiosulfate solution was applied to the entire surfaces of the leaves of the peanut plants on September 10 and 20 in a manner as described in Example 4. The peanuts were harvested on October 4. After that, the maturation acceleration effect of potassium thiosulfate was evaluated with respect to the peanuts.

The results are shown in the following Table 8.

TABLE 8

| | Total Yield | Pod Yield | | Seed Yield | | Percentages of Pod Yield based on |
| --- | --- | --- | --- | --- | --- | --- |
| Area | (kg/a) | (kg/a) | (%) | (kg/a) | (%) | Total Yield |
| Control Area | 101.0 | 48.5 | 100 | 27.8 | 57.8 | 48.0 |
| Sprayed Area | 102.5 | 53.4 | 110 | 33.0 | 61.9 | 52.1 |

As is clear from the results shown in Table 8, the pod yield and the seed yield were increased in the sprayed area compared to those in the control area.

Example 7

Radishes (variety: Gunma Riso #1) were seeded on September 6 and a 0.15% aqueous potassium thiosulfate solution was applied to the entire surfaces of the leaves of the radish plants on November 8 and 18 in a manner as described in Example 4. The radishes were harvested on November 28. After that, the maturation acceleration effect of potassium thiosulfate was evaluated with respect to the radishes. The results are shown in the following Table 9.

TABLE 9

| Area | Total Yield (kg/10 a) | Root Yield (kg/10 a) | (%) |
|---|---|---|---|
| Control Area | 10022 | 6812 | 100 |
| Sprayed Area | 10934 | 7629 | 112 |

As is clear from the results as shown in Table 9, the root yield in the sprayed area was remarkably higher than the yield in the control area.

Example 8

Tomatoes (variety: Raiden) were planted on May 29 and a 0.15% aqueous potassium thosulfate solution was applied to the entire surfaces of the leaves of the tomatoe plants every 10 days from July 14 till in a manner as described in Example 4. The crops were harvested between July 24 and September 30. After that, the maturation acceleration effect of potassium thiosulfate was evaluated with respect to the tomatoes. The results are shown in the following Table 10.

TABLE 10

| Area | Yield (kg/10 a) | | | |
|---|---|---|---|---|
| | July and August | September | Total | (%) |
| Control Area | 5070 | 2349 | 7419 | (100) |
| Sprayed Area | 5900 | 2820 | 8720 | (118) |

As is clear from the results shown in Table 10, the yield in the sprayed area was remarkably higher than the yield of the control area.

Example 9

Water melons (variety: Tenryu #2, stock: Aioi) were planted on April 25 and a 0.15% aqueous potassium thiosulfate solution was applied to the entire surfaces of the leaves of the water melon plants on July 1 and 11 in a manner as described in Example 4, so that, the maturation acceleration effect of potassium thiosulfate was evaluated with respect to the water melons. The crops were harvested on July 21. The results are shown in the following Table 11.

TABLE 11

| Area | Sugar Content (%) | | | Yield (First Crops) | |
|---|---|---|---|---|---|
| | Center | Seed Portion | Peel Portion | Number/10 a | (%) |
| Control Portion | 11.5 | 10.3 | 7.8 | 364 | (100) |
| Sprayed Portion | 12.0 | 10.8 | 8.0 | 412 | (113) |

As is clear from the results shown in Table 11, the yield as well as the sugar content of the fruits in the sprayed area were higher than those of the control area.

EXAMPLE 10

Carrots (variely: Tankon carrot) were seeded on July 10 and a 0.15% aqueous potassium thiosulfate solution was applied to the entire surfaces of the leaves of the carrot plants on October 25 and November 6 in a manner as described in Example 4. Thus, the maturation acceleration effect of potassium thiosulfate was evaluated with respect to the carrots. The crops were harvested on November 16. The results are shown in the following Table 12.

TABLE 12

| | Standard Carrot (On Average of 10 Samples) | | | | |
|---|---|---|---|---|---|
| | Root Length | Root Diameter | Root Weight | Yield per 66 m$^2$ | |
| Area | (cm) | (cm) | (g) | (kg) | (%) |
| Control Area | 10.3 | 6.1 | 198 | 21.9 | (100) |
| Sprayed Area | 12.2 | 6.2 | 220 | 25.7 | (117) |

As is clear from the results shown in Table 12, the yield in the sprayed area was remarkably higher than the yield in the control area. In addition, it was observed that the amount of the superior grade carrots obtained in the sprayed was higher than that in the control area.

EXAMPLE 11

Burdocks (variety: Yanagawa Risou) were seeded on April 17 and a 0.15% aqueous potassium thiosulfate solution was applied to the entire surface of the leaves of the burdock plants on September 15 and 30 in a manner as described in Example 4. The burdocks were harvested on October 15. After that, the maturation acceleration effect of potassium thiosulfate was evaluated with respect to the burdocks. The results are shown in the following Table 13.

TABLE 13

| Area | Yield (kg/10a) | (%) |
|---|---|---|
| Control Area | 2490 | (100) |
| Sprayed Area | 2547 | (102) |

As is shown in Table 13, the yield in the sprayed area was higher than the yield in the control area.

EXAMPLE 12

Konnyaku-imo (variety: Zairai Ninensei) were planted on May 3 (80 plants or 40 kg per each area having a size of 72 m$^2$) and a 0.15% aqueous potassium thiosulfate solution was applied to the entire surfaces of the leaves of the konnyaku-imo plants on September 3 and 18 in a manner as described in Example 4. The crops were harvested on October 3. After that, the maturation acceleration effect of potassium thiosulfate was evaluated with respect to the konnyaku-imo. The results are shown in the following Table 14.

TABLE 14

| Area | Tuber | | | | | Seed | | | |
|---|---|---|---|---|---|---|---|---|---|
| | Number | Total weight (kg) | Average weight (g) | Yield percentage (%) | Enlargement Ratio (times) | Number | Total weight (kg) | Average weight (g) | Yield percentage (%) |
| Control Area | 78 | 10.76 | 138 | 100 | 269 | 149 | 0.95 | 6.4 | 100 |
| Sprayed Area | 77 | 11.55 | 150 | 107 | 289 | 171 | 1.05 | 6.1 | 111 |

As is clear from the results shown in Table 14, the yields of tuber and seed in the sprayed area were remarkably increased compared to those the control area.

EXAMPLE 13

In order to evaluate the maturation acceleration effect of potassium thiosulfate with respect to pears, a 0.15% aqueous potassium thiosulfate solution was applied on the surfaces of the leaves of pear trees (variety: Nijyusseiki) by using a spraying machine on August 24 and September 4, in such a manner that the entire surfaces of the leaves were uniformly wetted. The pears were harvested on September 14. The results are shown in the following Table 15.

TABLE 15

| Area | Number of Sample Fruits | Average weight (g) | Average sugar content (%) | Average Hardness | PH | Grade Excellent | Good | Fair |
|---|---|---|---|---|---|---|---|---|
| Control Area | 20 | 304 | 10.28 | 0.92 | 4.3 | 15 | 3 | 2 |
| Sprayed Area | 20 | 318 | 11.14 | 0.81 | 4.3 | 18 | 2 | 0 |

As is clear from the results shown in Table 15, in the sprayed area, fruit haivng a better sugar content were obtained compared to the control field. In addition, the yield of excellent grade was higher in the sprayed area.

EXAMPLE 14

In order to evaluate the maturation acceleration effect of potassium thiosulfate with respect to chestnuts, a 0.15% aqueous potassium thiosulfate solution was applied to chestnut trees (variety: Tanzawa Rokunensei) on August 8 and 18 in a manner as described in Example 13. The chestnuts were harvested between August 28 and September 7. The results are shown in the following Table 16.

TABLE 16

| Area | Yield (kg/10a) | | | | | |
|---|---|---|---|---|---|---|
| | LL | L | M | S | Total | (%) |
| Control Area | 7 | 38 | 62 | 36 | 143 | (100) |
| Sprayed Area | 18 | 76 | 42 | 14 | 150 | (105) |

As is clear from the results shown in Table 16, the yield in the sprayed area was increased and, especially, the yield of the large size grades LL and L was remarkably increased compared to the control area.

EXAMPLE 15

In order to evaluate the maturation acceleration effect of potassium thiosulfate with respect to apples, a 0.15% aqueous potassium thiosulfate solution was applied to apple trees (variety: thirty year old Iwai) on June 25 and July 5 in a manner as described in Example 13. The apples were harvested between July 15 and August 1. The results are shown in Example 13. The apples were harvested between July 15 and August 1. The results are shown in the following Table 17.

TABLE 17

| Area | Sugar Content (%) (On average of 20 Samples) | Yield (3 Test Trees) | | |
|---|---|---|---|---|
| | | Number Fruit | weight (kg) | % |
| Control Area | 9.8 | 2091 | 351 | 100 |
| Sprayed Area | 10.0 | 2315 | 394 | 112 |

As is clear from the results shown in Table 17, the yield in the sprayed area was remarkably increased and the sugar content was somewhat increased, compared to the control area. In addition, it was observed that the harvesting season in the sprayed area was somewhat accelerated compared to the control area.

EXAMPLE 16

In order to evaluate the maturation acceleration effect of potassium thiosulfate with respect to persimmons, a 0.15% aqueous potassium thiosulfate solution was applied to persimmon trees (variety: eleven year old Sanjya Gaki) on October 10 and 20 in a manner as described in Example 13. The persimmons were harvested between October 28 and November 4. The results are shown in the following Table 18.

TABLE 18

| Area | Number of Fruits (per 1 Tree) | Sugar Content (%) on Average (20 fruits) | Yield (kg/Tree) | Average Weight (g/fruit) | Percentage (%) | |
|---|---|---|---|---|---|---|
| | | | | | Yield | Average Weight |
| Control Area | 461 | 17.3 | 131 | 284 | 100 | 100 |
| Sprayed Area | 480 | 17.3 | 146 | 304 | 111 | 107 |

(Remarks)
Cultivated Trees: 36 trees/10 a,
Test Tress: 3 trees/each area

As is clear from the results shown in Table 18, the weight of one persimmon was increased and, especially, the total yield of the persimmons obtained was remarkably increased in the sprayed area, compared to the control area.

EXAMPLE 17

Waterfield rice plants (variety: Nihonbare) were transferred to a test pot on May 9 and a 15% potassium thiosulfate solution was applied to the waterfield rice plants on August 25 and September 1 in a manner as described in Example 13. The results are shown in the following Table 19.

TABLE 19

| Area | Maturation Time | | | | | Yield | | |
|---|---|---|---|---|---|---|---|---|
| | Heading Time | Full Ripened Time | Stem Length (cm) | Ear Length (cm) | Number of Ear (Number/m$^2$) | Straw Weight (kg/a) | Rice Weight (kg/a) | Weight of Thousand Grains (g) |
| Control Area | Aug. 11 | Oct. 8 | 84.2 | 20.2 | 512 | 78 | 66.3 | 21.1 |
| Sprayed Area | Aug. 11 | Oct. 7 | 83.8 | 20.1 | 511 | 76 | 67.4 | 21.6 |

As is clear from the results shown in Table 19, the thousand grain weight was remarkably increased and the straw weight was decreased in the sprayed area, compared to the control area. As a result, the unhulled rice weight in the sprayed area was increased. It was observed that there were no substantial difference in the stem length and the length and the number of the ears between the sprayed area and the control area.

I claim:

1. A method for accelerating the maturation of field and garden crops from which fruits, seeds, roots or subterranean stems are harvested, said method comprising applying an aqueous solution, having a concentration of from 0.01 to 0.3% by weight, of at least one thiosulfate selected from the group consisting of potassium thiosulfate, soduium thiosulfate, magnesium thiosulfate and ammonium thiosulfate to the crops immediately before the change of stage in plant physiology between the nutritive growth stage and the maturation stage.

2. A method as claimed in claim 1, wherein said field and garden crops are fruit trees, fruit vines, fruit vegetables, edible roots, pulse crops, grains and feed crop plants.

* * * * *